(12) United States Patent
Horter et al.

(10) Patent No.: US 10,835,736 B2
(45) Date of Patent: Nov. 17, 2020

(54) EMS EXERCISE DEVICE, EMS ELECTRODE, EMS GARMENT, EMS STIMULUS GENERATING UNIT, EMS SIGNAL CABLE, AND EMS UNDERGARMENT FOR AN EMS EXERCISE DEVICE, AND METHOD FOR OPERATING THE EMS EXERCISE DEVICE

(71) Applicant: Miha Bodytec GmbH, Gersthofen (DE)

(72) Inventors: Hansjürgen Horter, Oberboihingen (DE); Peter Österreicher, Wernau (DE); Jürgen Decker, Emersacker (DE); Jonas Peinze, Wangen in Allgäu (DE)

(73) Assignee: Miha Bodytec GmbH, Gersthofen (DE)

( * ) Notice: Subject to any disclaimer, the term of this patent is extended or adjusted under 35 U.S.C. 154(b) by 507 days.

(21) Appl. No.: 15/450,018

(22) Filed: Mar. 5, 2017

(65) Prior Publication Data
US 2017/0173324 A1 Jun. 22, 2017

Related U.S. Application Data

(63) Continuation of application No. PCT/EP2015/025054, filed on Jul. 31, 2015.

(30) Foreign Application Priority Data

Sep. 5, 2014 (DE) .......................... 10 2014 012 920

(51) Int. Cl.
*A61N 1/04* (2006.01)
*C23F 13/10* (2006.01)
(Continued)

(52) U.S. Cl.
CPC .............. *A61N 1/0484* (2013.01); *A41B 1/08* (2013.01); *A41B 9/00* (2013.01); *A41D 1/002* (2013.01);
(Continued)

(58) Field of Classification Search
CPC .. A61N 1/0492; A61N 1/0484; A61N 1/0452; A61N 1/36003; A61N 1/36014
See application file for complete search history.

(56) References Cited

U.S. PATENT DOCUMENTS 3,610,250 A 10/1971 Sarbacher
3,662,757 A 5/1972 Blackett
(Continued)

FOREIGN PATENT DOCUMENTS

CN 200980675 11/2007
DE 2018239 11/1970
(Continued)

OTHER PUBLICATIONS

International Search report issued in PCT/EP2015/025054, on which this application is based, dated Oct. 30, 2015.
(Continued)

*Primary Examiner* — George R Evanisko
(74) *Attorney, Agent, or Firm* — Falk Ewers; Ewers IP Law PLLC

(57) ABSTRACT

An EMS exercise device is provided which includes EMS electrodes and at least one sacrificial anode, preferably a dedicated sacrificial anode for each EMS electrode. The at least one sacrificial anode is connected to the EMS electrodes in an electrically conductive manner in order to protect the EMS electrodes and/or other elements in the electrically conductive connections from corrosion. In addition, an EMS electrode with a sacrificial anode, an EMS garment a sacrificial anode, an EMS signal cable a sacrificial
(Continued)

anode, an EMS pulse generating unit a sacrificial anode, and an EMS undergarment with a sacrificial anode for an EMS exercise device are provided, and a method for operating an EMS exercise device, for which a sacrificial anode is provided.

8 Claims, 4 Drawing Sheets

(51) Int. Cl.
    *A41B 1/08*     (2006.01)
    *A41B 9/00*     (2006.01)
    *A41D 1/00*     (2018.01)
    *A41D 3/00*     (2006.01)
    *A41D 13/00*     (2006.01)
    *A41D 20/00*     (2006.01)
    *A41F 9/00*     (2006.01)
    *A61N 1/36*     (2006.01)

(52) U.S. Cl.
    CPC ........... *A41D 3/00* (2013.01); *A41D 13/0015* (2013.01); *A41D 20/00* (2013.01); *A41F 9/002* (2013.01); *A61N 1/048* (2013.01); *A61N 1/0452* (2013.01); *A61N 1/0488* (2013.01); *A61N 1/0492* (2013.01); *A61N 1/36003* (2013.01); *A61N 1/36014* (2013.01); *C23F 13/10* (2013.01); *C23F 2213/30* (2013.01)

(56) References Cited

U.S. PATENT DOCUMENTS

| | | | |
|---|---|---|---|
| 4,729,377 A | 3/1988 | Granek et al. | |
| 5,285,781 A | 2/1994 | Brodard | |
| 6,019,877 A * | 2/2000 | Dupelle | A61N 1/0492 204/196.11 |
| 6,845,272 B1 | 1/2005 | Thomsen et al. | |
| 7,097,746 B1 * | 8/2006 | Tziviskos | H01R 9/0518 204/196.23 |
| 9,067,199 B2 | 6/2015 | Nesterenko et al. | |
| 2002/0077688 A1 | 6/2002 | Kirkland | |
| 2002/0077689 A1 | 6/2002 | Kirkland | |
| 2002/0099320 A1 * | 7/2002 | Beck | A61N 1/044 604/20 |
| 2004/0009731 A1 | 1/2004 | Rabinowicz | |
| 2005/0246002 A1 | 11/2005 | Martinez | |
| 2009/0105795 A1 | 4/2009 | Minogue et al. | |
| 2010/0228113 A1 * | 9/2010 | Solosko | A61B 5/0416 600/382 |
| 2012/0172940 A1 * | 7/2012 | Wahls | A41D 1/005 607/3 |
| 2015/0202429 A1 | 7/2015 | Fritsche | |

FOREIGN PATENT DOCUMENTS

| | | |
|---|---|---|
| DE | 20209219 U1 | 10/2002 |
| DE | 10248235 A1 | 5/2004 |
| DE | 202004004582 U1 | 6/2004 |
| DE | 102005058850 A1 | 6/2007 |
| DE | 102007046886 A1 | 4/2009 |
| DE | 102009017179 A1 | 12/2010 |
| DE | 202011050682 U1 | 11/2011 |
| DE | 202011109226 U1 | 8/2012 |
| DE | 102012112153 A1 | 6/2014 |
| EP | 0128103 A1 | 12/1984 |
| EP | 0459945 B1 | 12/1991 |
| EP | 0965358 A2 | 12/1999 |
| EP | 2024020 A1 | 2/2009 |
| WO | 2004006700 A1 | 1/2004 |
| WO | 2005107849 A1 | 11/2005 |
| WO | 2007138071 A1 | 12/2007 |
| WO | 2011/089263 A1 | 7/2011 |
| WO | 2011118918 A2 | 9/2011 |
| WO | 2014/000736 A2 | 1/2014 |

OTHER PUBLICATIONS

U.S. Appl. No. 15/604,532, filed May 24, 2017, Hansjürgen Horter.
U.S. Appl. No. 15/618,015, filed Jun. 8, 2017, Jürgen Decker.

* cited by examiner

EMS EXERCISE DEVICE, EMS ELECTRODE, EMS GARMENT, EMS STIMULUS GENERATING UNIT, EMS SIGNAL CABLE, AND EMS UNDERGARMENT FOR AN EMS EXERCISE DEVICE, AND METHOD FOR OPERATING THE EMS EXERCISE DEVICE

CROSS REFERENCE TO RELATED APPLICATIONS

This application is a continuation application of international patent application PCT/EP2015/025054, filed Jul. 31, 2015, designating the United States and claiming priority from German application 10 2014 012 920.9, filed Sep. 5, 2014, and the entire content of both applications is incorporated herein by reference.

TECHNICAL FIELD

The present disclosure relates to an EMS exercise device, an EMS electrode, an EMS garment, an EMS stimulus generating unit, an EMS signal cable, and an EMS undergarment. The present disclosure furthermore relates to a method for operating the EMS exercise device.

BACKGROUND

Electrical muscle stimulation (EMS), sometimes also called electromyostimulation, is generally used to apply electrical stimuli to muscles in the living body, for example in fitness studios to build muscles or with personal trainers to strengthen the muscles.

In this case, conventional EMS electrodes to be applied to the body frequently have textile structures or textile structure sections with incorporated metal threads, in particular silver or copper metal threads, or polymer pads, which are filled with conductive particles (for example, carbon black). An EMS electrode is described, for example, in German patent application DE 10 2007 046 886 A1.

Such EMS electrodes are usually wetted before exercise or worn over a wetted undergarment, for example, a T-shirt, for which purpose they are generally attached to an electrode carrier applicable to the body. While earlier electrode carriers frequently consisted of belts and leather straps, to which the electrodes were attached, development is going more and more towards EMS garments, in particular textile garments, which support the electrodes and which can be worn by the exercising person like a garment, i.e., for example, as a vest, as pants, as stockings, as a wristband, or the like. To further increase the acceptance of electrical muscle stimulation (EMS) in this case, an attempt is made to better integrate the electrodes and the conductor tracks connected to the electrodes into the EMS garment and to thus eliminate the visible cables or at least to shorten the cables leading from the EMS garment to an external control unit, and also to make the electrodes not only invisible as much as possible, but rather also to increase the wearing comfort of the EMS garment in general, in that the EMS electrodes are made as flexible and elastic as possible, frequently from textile materials. One example of such an EMS garment is described in German patent DE 10 2009 017 179 B4. A further EMS garment having adhesively-bonded, textile EMS electrodes is described in utility model specification DE 20 2011 050 682 U1.

There are already battery-operated EMS stimulus generating units, which form the EMS stimuli to be emitted via the EMS electrodes to the body and which can therefore be worn directly on the EMS garment and thus "autonomously" on the body. See DE 20 2011 109 226 U1, WO 2011/089 263 A2, and WO 20141000 736 A2. However, the battery power is generally not sufficient to generate these EMS stimuli, which consist of current pulses and/or alternating current, over a period of time acceptable in exercise operation. The EMS stimulus generating unit generally has an electrical pulse generator for generating these EMS stimuli, and also an electronic controller, which specifies an excitation scheme, according to which a plurality of EMS stimuli, which are distributed chronologically and onto the EMS electrodes of the EMS exercise device, is formed from a current acquired from a current source, said stimuli consisting of the current pulses and/or alternating current having values specified via the controller, such as amplitude and frequency, and which are applied to the EMS electrodes, to conduct current having predefined amplitude and frequency pattern through the body. In this case, the EMS electrodes are typically grouped in pairs on the EMS garment, so that two EMS electrodes grouped into such a pair are each connected via one line branch to the EMS stimulus generating unit, which are connected to form a closed circuit during the EMS exercise by the body to which they are applied, said circuit leading through the body and therefore through the muscles.

Of course, this current flow can be substantially more complex if more than one pair of electrodes are used and can include current flows between more than two different EMS electrodes. Furthermore, a wetted garment is routinely worn under the EMS garment or the electrode carrier having the EMS electrodes, often a commercially available T-shirt, for example, wherein in the meantime EMS undergarments have also become available, which are optimized for through conduction of the currents forming the EMS stimuli and for absorbency, and accordingly are also interconnected in the circuit. In this case, the EMS electrodes are generally connected in pairs so that at one point in time a pulse current is applied to one EMS electrode and is not applied to the other electrode at this point in time, wherein the two line branches leading to the body come into contact with the water typically used for wetting the EMS electrodes and the sweat on the skin surface. Upon a pulse change, a pulse of current is applied to the other EMS electrode and not to the first electrode.

As can be inferred, for example, from German patent application DIE 102 48 235 A1, the line branches which connect the EMS electrodes to the EMS stimulus generating unit are funned in this case at least between a terminal point on the EMS garment and the EMS stimulus generating unit as an EMS signal cable, which leads from an EMS stimulus generating unit, which is typically arranged remotely from the exercising person and therefore from the EMS garments which are worn, directly to the EMS electrodes or to corresponding terminals on the EMS garment or garments. The EMS stimulus generating unit is typically housed in this case in a control unit having a user interface, frequently in the form of a control panel, and connected to the regular power grid. Such a control unit can be inferred in principle, although at the technical level of the beginning of the 1990s, from European patent specification EP 0 459 945 B1. Such EMS exercise devices are produced by various manufacturers and are operated professionally in fitness studios by personal trainers, etc., but also directly by end-consumers.

While the successes of the EMS method in building muscles are undisputed and EMS exercise devices are encountering greater and greater interest with the public because of the more and more improved external appearance, systemic problems are also more clearly coming to light as a result of the increased usage. For example, unexplainable failures of EMS electrodes occur randomly with respect to time, occur in use, which results, in the case of the present EMS garments, in which the electrodes are already integrated, in the replacement of the entire EMS garment, i.e., for example, an exercise vest. Electrode failure in this context means that the affected EMS electrode no longer emits a pulse current or sufficient pulse current to the body, although no current line or contact point between the EMS electrode and the EMS stimulus generating unit, which applies current to the EMS electrode, has to be broken and the electrode also does not have to have an externally visible defect.

SUMMARY

Proceeding therefrom, it is an object of the present invention to provide an EMS electrode, an EMS garment, an EMS stimulus generating unit, an EMS signal cable, an EMS undergarment, an EMS exercise device, and a method for operating an EMS exercise device, in which the functionality of the EMS electrodes or EMS garments used in the EMS exercise device can be ensured over a long period of time.

According to an aspect of the invention, a method is provided, in which, in the circuit, which is closed from the EMS stimulus generating unit via an EMS signal cable and an EMS electrode, the sweat located on the skin surface of the exercising person, the skin surface itself, and the body interior and back out from the body interior through the skin and the sweat located on the skin to a further EMS electrode and from there via a corresponding EMS signal line back to the EMS stimulus generating unit, a sacrificial anode is preferably introduced on both sides of the body. Furthermore, an EMS exercise device is provided, in which the sacrificial anode(s) is/are introduced into the circuit. Furthermore, auxiliary means are provided according to an aspect of the invention, to introduce the sacrificial anode(s) there, namely an EMS electrode having the sacrificial anode(s), an EMS garment having the sacrificial anode(s), an EMS signal, cable having the sacrificial anode(s), and an EMS undergarment having the sacrificial anode(s).

The invention is based on the finding in this case that different, also temporarily different resistances can occur in the line branch leading from the EMS stimulus generating unit via the first EMS electrode to the body in comparison to the line branch leading via the second EMS electrode back to the EMS stimulus generating unit. These resistances are induced by chronologically changing conditions in the circuit, for example, the contact of differing quality of the respective EMS electrode on the body, sweat separation occurring to different extents locally on the skin surfaces wetting to different extents of the two EMS electrodes, etc., but also by systemic errors, for example, at the connecting points of the EMS electrodes to EMS signal connecting cables, which are frequently designed as snaps or crimp plugs. Due to these resistance differences, oxidation, and as a result corrosion, occurs at different locations in the circuit, wherein the metallic material provided there oxidizes and therefore corrodes at the corroding points with electron emission.

The build-up of an intermediate resistance is thus caused from an electrical viewpoint at the corroding points, which can go far enough over time that the EMS electrode arranged in the affected line branch can no longer transmit the EMS stimulus required for the desired muscle contraction.

If this line branch is electrically conductively connected to a sacrificial electrode, instead of the EMS electrode, a connection point of EMS electrode and EMS signal cable or other susceptible points in the line branch, the sacrificial anode itself corrodes, i.e., it sacrifices itself until it is completely corroded. The service life of the EMS equipment, i.e., the EMS electrodes or the costly EMS garment, which acts as a carrier for the EMS electrodes, may thus be extended until it has reached its cost-effective usage duration as result of other routine wear.

In this case, each EMS electrode or each line branch from the EMS stimulus generating unit to the respective EMS electrode is advantageously assigned a separate sacrificial anode, i.e., the sacrificial anode is electrically conductively connected to the respective line branch. However, it is also conceivable to provide a shared sacrificial anode for multiple line branches and to conductively connect it to multiple line branches, for example to those which are charged in common mode with EMS stimuli, i.e., with current pulses, of even—with appropriate wiring and/or appropriate circuitry—in a star shape to all line branches. It is even possible as a result of the complex current flows in a current EMS exercise device having a plurality of EMS electrodes to achieve the above-described corrosion protection effect without all line branches being directly connected to a sacrificial anode.

While the selection of the material tier the sacrificial anode is limited to a material having a more negative standard electrode potential than the material used for the electrically conductive parts of the EMS electrode and the electrically conductive connection between the EMS stimulus generating unit and the EMS electrode, i.e., in general to a material and in particular a metal having a negative standard electrode potential in the electrochemical electromotive series. For reasons of cost and processing, preferably magnesium or magnesium alloys, and for reasons of skin compatibility, advantageously no nonferrous metal is used. However, the choice of the attachment location of the sacrificial anode is substantially free, as long as the sacrificial anode is connected to the EMS electrodes or line branches to be protected.

The closer the sacrificial anode is arranged, however, to the electrically conductive material which tends toward oxidation, the better is the effect. The material which tends toward oxidation is generally located in this case on the EMS electrode, at a contact point (snap), or in the line. Experiments have also shown that an advantageous position for the sacrificial anode(s) is directly on the EMS electrode(s). As long as each EMS electrode or each line branch which leads from the EMS stimulus generating unit to one of the EMS electrodes is assigned a separate sacrificial anode, and each line branch is connected to its sacrificial anode, however, this sacrificial anode can at least theoretically be attached anywhere in the entire region of this line branch or even remotely therefrom. Moreover, the sacrificial anode can be connected to a corresponding electrical line at any suitable point on the line branch if the electrical resistances of the connection are very low and no interruptions arise.

Further suitable points for attaching the sacrificial anode(s) are the snaps, at which leads of the power cable are fastened on the EMS garment or on the EMS electrode, typically by soldering, sewing, or clamping on between the two parts of the snap, and/or a woven fabric, crocheted fabric, or knitted fabric, which forms a conductive layer of the EMS electrode, including metallic or metallized threads (for example, silver threads or silver-containing threads). A sacrificial anode formed as a metal plate or strip can simply be adhesively bonded thereon, wherein the electrical terminal may be produced cost-effectively on the respective line branch in a simple manner.

A further rapid and simple fastening of the sacrificial anode is riveting on, preferably on the snap on the EMS garment or on the EMS electrode. In this case, the plate-shaped sacrificial anode can be riveted on by one or more other rivets or can itself be formed as a rivet and can be riveted on.

The sacrificial anode could also be formed in this case as a magnesium-containing paint or imprint on the snap of the line terminal or at another suitable location in the line branch. A magnesium-containing coating would also be conceivable. Weaving or sewing magnesium-containing textile sections or the like, or also a corresponding metal plate, into a textile section of the assigned EMS electrode is also conceivable.

It is further conceivable to also insulate the sacrificial anode under the insulation of a lead in an EMS signal cable, for example, in the form of a magnesium foil wrapped coaxially around the lead, wherein the EMS signal cable is equipped with corresponding terminals for the connection to an EMS stimulus generating unit or a control unit having the EMS stimulus generating unit and an EMS electrode or an EMS garment, for example, on the side of the EMS garment or the EMS electrode with a counter snap which can be pressed onto the snap provided there and on the side of the control unit with a corresponding plug. The sacrificial anode or the sacrificial anodes could also be provided, however, directly on the control unit or the EMS stimulus generating unit(s).

In this case, the durability of the EMS electrodes or the feed line having the EMS electrodes may be increased still further beyond the service life of the sacrificial anode if the sacrificial anodes are attached in a replaceable manner the device side, for example, by providing a corresponding slot for a replaceable insert part, on which the sacrificial anode or anodes are connected to the respective EMS stimulus generating unit. Of course, it is also possible to provide a pocket closable by a hook-and-loop closure, for example, on an EMS electrode, into which a metal plate used as the sacrificial anode could be inserted, which is electrically conductively connected to a conductive layer of the electrode at least upon wetting of the electrode or via textile-integrated conductors which touch the sacrificial electrode. The pocket then forms the slot and the sacrificial anode metal plate forms the replaceable insert part. It is also possible to coat the EMS electrode using a gel, or to introduce such a gel into the pocket, which has sacrificial anode properties and therefore forms the sacrificial anode.

A further possibility for introducing a sacrificial anode into the circuit, which is closed from the EMS stimulus generating unit via the two EMS electrodes assigned to one another and back to the EMS stimulus generating unit, or into one of the two line branches is to provide the liquid used for wetting the EMS electrodes alternatively or additionally to the above-described solid-state sacrificial anodes—with particles, which have the desired sacrificial anode property of a negative standard electrode potential in the electrochemical electromotive series and then oxidize instead of the conductor metal in the EMS electrodes or the feed lines thereof and are transported away via sweat after the exercise, or remain in an undergarment, which is worn in most cases under the EMS electrodes.

It is also conceivable to equip such an EMS undergarment which is to be worn under the EMS electrodes or under the EMS garment, with one or an appropriate number of sacrificial anodes positioned at the correct points. In this case, at least one sacrificial anode for each line branch is advantageously integrated into the EMS undergarment so that an electrically conductive connection to the assigned EMS electrode is established via the sweat-wet and/or previously-wetted EMS undergarment. The sacrificial anode can advantageously be formed in this case as a metal plate or strip and can be mounted via textile on the EMS undergarment, for example, embroidered or sewn on. However, it can also be attached as a rivet to the EMS undergarment. The EMS electrode is in this case advantageously located directly under a position provided for an associated EMS electrode.

It can be seen that the general concept of the invention of providing a sacrificial anode in the circuit or circuits of the EMS exercise device, which close during the EMS exercise between one or more EMS stimulus generating units and the exercising body, is manifested on a variety of subjects which can be handled separately and implementable methods, which have each been made the subject matter of individual, concurrent claims.

The invention therefore relates to an EMS electrode for transmitting EMS stimuli, which are formed by current pulses and/or alternating current having predefined values such as amplitude and frequency, from a connected EMS stimulus generating unit to the living body, wherein the EMS electrode has a plane pad applied flexibly to the body or a textile structure section having an electrically conductive conducting section, in particular having a textile conducting section containing metallic or metallized threads. The EMS electrode according to an aspect of the invention is distinguished in that it carries a sacrificial anode, which is electrically conductively connected or connectable to the conductive layer. The sacrificial anode consists of a material, preferably a metal, having a negative standard electrode potential in the electrochemical electromotive series, or includes such a material, in particular magnesium, but is advantageously free of nonferrous heavy metal, for example, nickel.

The invention furthermore relates to an EMS garment, for example, a sun, a jacket, a belt, a shirt, a pair of pants, a wristband, and/or a leg band, which carries a first number of EMS electrodes, in particular a plurality of EMS electrodes, and which is in particular a textile, wherein the first number of EMS electrodes, in particular the plurality of EMS electrodes for transmitting EMS stimuli consisting of current pulses and/or alternating current having predefined values such as a predefined amplitude value and a predefined frequency value from a connected EMS stimulus generating unit to the living body, are each designed as a plane pad applied flexibly to the body or as a textile structure section having an electrically conducting conductive layer, in particular having a textile conductive layer containing metallic or metallized threads. The EMS garment according to an aspect of the invention has at least one sacrificial anode, preferably a separate sacrificial anode for each EMS electrode, which is electrically conductively connected to the respective EMS electrode, wherein the sacrificial anode consists of or contains a material, preferably a metal, having a negative standard electrode potential in the electrochemical electromotive series or includes such a material, in particular magnesium or magnesium alloys, but is advantageously free of nonferrous heavy metal, for example, nickel.

The invention furthermore relates to an EMS stimulus generating unit, which has terminals for a number of EMS electrodes connectable via EMS signal cables and which is configured to form a sequence of EMS stimuli which follows a predefined excitation scheme for the number of connected EMS electrodes from a current acquired from a current source, wherein the sequence of EMS stimuli consists of current pulses and/or an alternating current having predefined values such as a predefined amplitude value and a predefined frequency value. The EMS stimulus generating unit according to an aspect of the invention has at least one electrically conductively connected sacrificial anode preferably a separate anode for each connectable EMS electrode, which consists of or contains a material, preferably a metal, having a negative standard electrode potential in the electrochemical electromotive series or includes such a material, in particular magnesium or magnesium alloys, but is advantageously free of nonferrous heavy metal, for example, nickel, wherein the sacrificial anode is designed in particular as a metal plate or strip attached to a terminal for an EMS signal cable or as a molded part adapted to the terminal.

The invention furthermore relates to an EMS signal cable configured for connecting an EMS electrode that can be attached to a living body to at least one EMS stimulus generating unit and/or for transmitting EMS stimuli, which include current pulses and/or an alternating current having predefined values such as a predefined amplitude value or a predefined frequency value, from the EMS stimulus generating unit to the connected EMS electrode. The EMS signal cable according to an aspect of the invention has at least one electrically conductively connected sacrificial anode, which consists of or contains a material, preferably a metal having a negative standard electrode potential in the electrochemical electromotive series or includes such a material, in particular magnesium or magnesium alloys, but is advantageously free of nonferrous heavy metal, for example, nickel, wherein the sacrificial anode is designed in particular as a metal plate or strip attached to a terminal plug of the EMS signal cable, as a molded part adapted thereto, or as a coaxial ring which encloses a lead of the EMS signal cable.

The invention furthermore relates to an EMS undergarment to be worn under EMS electrodes or an electrode carrier or EMS garment having EMS electrodes, in which at least one sacrificial anode, preferably at least one anode for each EMS electrode provided for wearing on the EMS undergarment, is integrated into the EMS undergarment so that it is electrically conductively connected to the EMS electrode upon attachment of the EMS electrode at a point provided for this purpose on the EMS undergarment, which is applied to the body and which is in particular wet, wherein the sacrificial anode consists of or contains a material, preferably a metal, having a negative standard electrode potential in the electrochemical electromotive series or includes such a material, in particular magnesium or magnesium alloys, but which is advantageously free of a nonferrous heavy metal, for example, nickel, wherein the sacrificial anode is advantageously mounted in the textile as a metal plate or strip, for example, embroidered or sewn on or is attached as a rivet to the EMS undergarment, preferably in each case directly under a position provided for an assigned EMS electrode.

The invention furthermore relates to an EMS exercise device, having a third number of EMS electrodes, in particular a plurality of EMS electrodes attachable to the living body assigned to one another in pairs, for applying EMS stimuli to the body, a fourth number of EMS stimulus generating units which are electrically conductively connected to the third number of EMS electrodes, and which form a plurality of EMS stimuli, which follow a predefined excitation scheme and which are distributed sequentially and with respect to the electrodes, from a current acquired from a current source, which stimuli consist of current pulses and/or an alternating current having predefined values such as a predefined amplitude value and a predefined frequency value, and which are applied to the third number of EMS electrodes to conduct the current having a predefined amplitude and frequency pattern through the body, in particular between EMS electrodes assigned to one another in pairs. According to an aspect of the invention, in order to protect the third number of EMS electrodes and/or other elements in the electrically conductive connections from corrosion, the EMS exercise device has at least one sacrificial anode, preferably a separate one for each EMS electrode, which is electrically conductively connected to the EMS electrode, wherein each sacrificial anode consists of or contains a material, preferably a metal, having a negative standard electrode potential in the electrochemical electromotive series or includes such a material, in particular magnesium or magnesium alloys, but is advantageously free of nonferrous metal, for example, nickel, and wherein each sacrificial anode is preferably formed as a metal plate, strip, or molded part.

The invention furthermore relates to a method for operating an EMS exercise device. EMS electrodes, which are attachable to the living body, are each electrically conductively connected, for example, via an EMS signal cable, to the at least one EMS stimulus generating unit thereof, to form line branches, which are completed through the body to form one or more closed circuits during the EMS exercise, wherein in particular each pair of line branches are assigned to one another, to form a closed circuit extending through the body during the EMS exercise. The method according to an aspect of the invention is distinguished in that for EMS exercise, an EMS exercise device according to an aspect of the invention is provided, wherein the EMS exercise device is either already provided with the at least one sacrificial anode during the production thereof or is first retrofitted with the at least one sacrificial anode before and/or during the EMS exercise, in particular with at least one separate sacrificial anode in each circuit, preferably at least one separate sacrificial anode in each line branch. In this case, the sacrificial anode can preferably be formed as a metal plate or strip or molded part and/or at least one of the EMS electrodes can be wetted with a liquid and/or coated with a gel before and/or during the EMS exercise, in which particles are contained, in particular dissolved, which act as the sacrificial anode and for this purpose in particular consist of a material, preferably of a metal, having a negative standard electrode potential in the electrochemical electromotive series or includes such a material, in particular magnesium or magnesium alloys which is advantageously free of nonferrous heavy metal, for example, nickel, however.

BRIEF DESCRIPTION OF THE DRAWINGS

The invention will now be described with reference to the drawings wherein.

DESCRIPTION OF EXEMPLARY EMBODIMENTS

Figure 1:
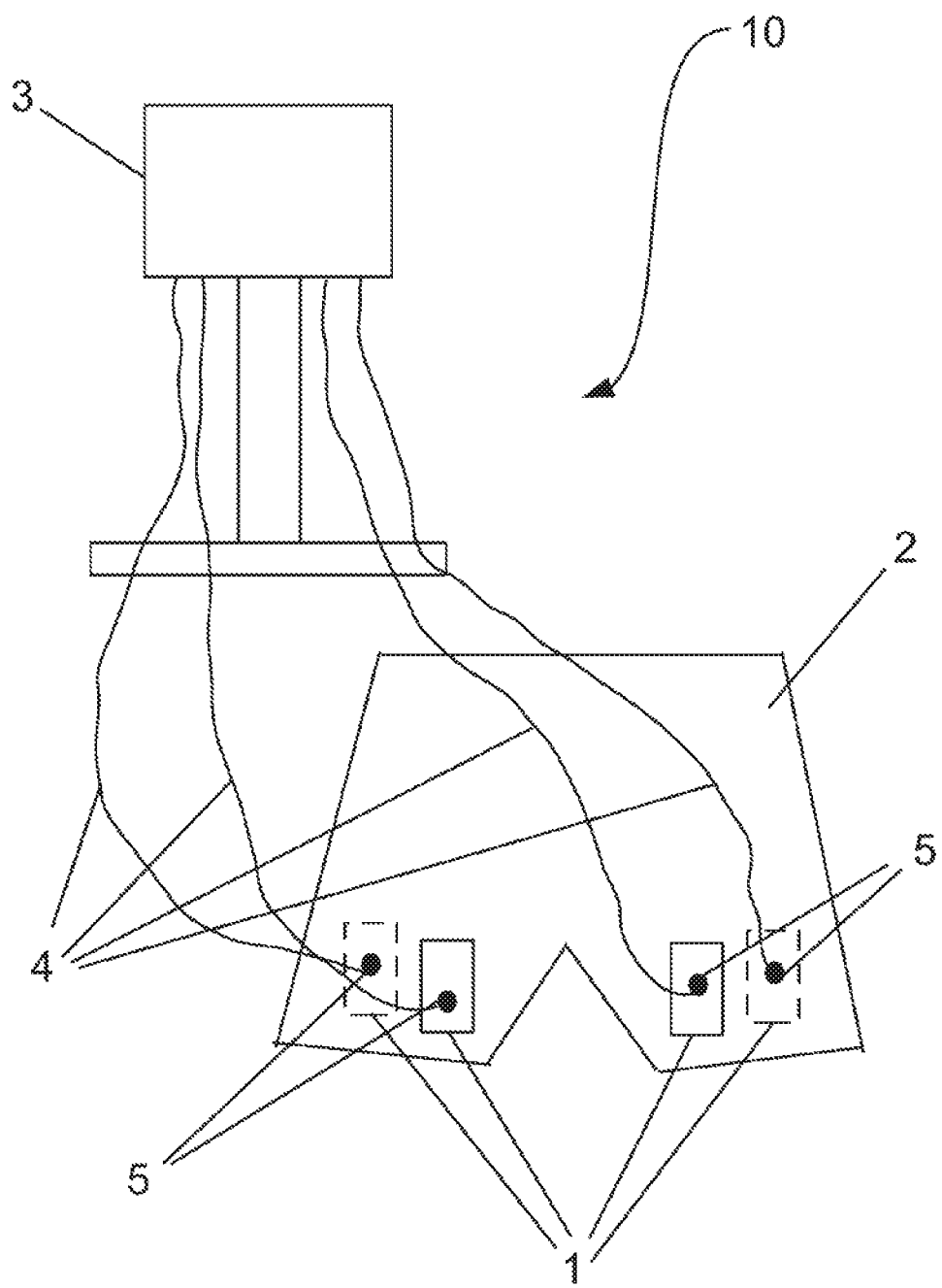
FIG. 1 shows a schematic view of an EMS exercise device.

FIG. 1 shows an EMS garment 2 designed as a pair of shorts, which is equipped with four EMS electrodes 1 respectively grouped into two pairs of EMS electrodes, wherein each pair of EMS electrodes is assigned to one thigh, and wherein each EMS electrode 1 is connected via an EMS signal cable 4 to an EMS stimulus generating unit which is installed in a control unit 3 in the form of a control panel. The EMS electrodes 1 have snaps 5 into which the EMS signal plugs 4 are plugged using corresponding plugs.

Figure 5:
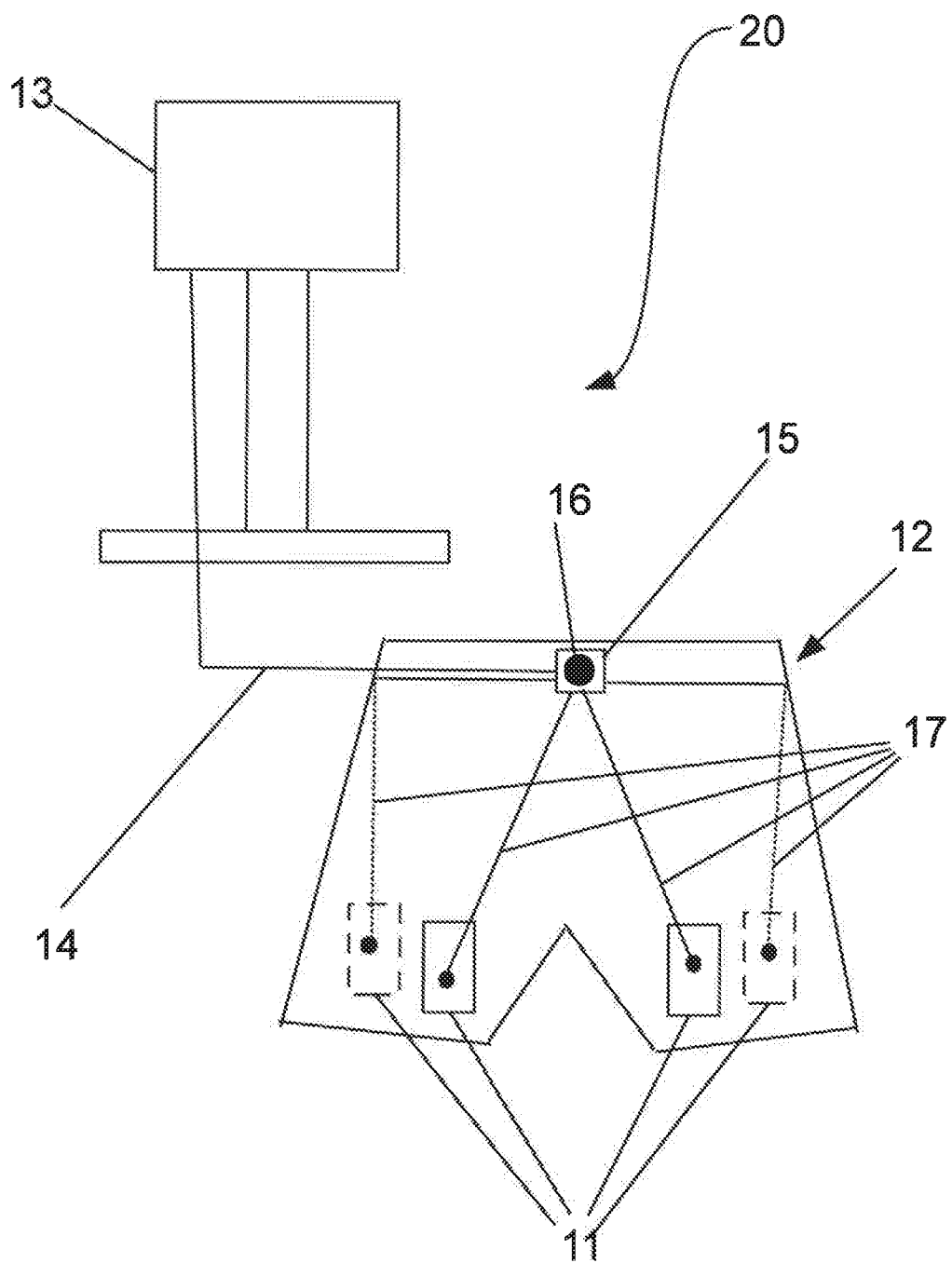
FIG. 5 shows a schematic view of an EMS exercise device according to an exemplary embodiment of the invention.

FIG. 5 shows an EMS garment 12 according to an exemplary embodiment of the invention. The EMS garment 12 is designed as short trousers, which is equipped with four EMS electrodes 11 respectively grouped into two pairs, wherein each electrode pair is assigned to one thigh. Each EMS electrode 11 is connected via an EMS signal line 17 to an electrical terminal 15 formed as a snap. The EMS signal lines 17 can be pressed to, sewn on, soldered on, or welded on the electrical terminal 15. A sacrificial anode 16 is riveted on the electrical terminal 15 formed as the snap. An EMS signal cable 14 connects the EMS garment 12 via its electrical terminal 15 to an EMS stimulus generating unit installed into a control unit 13 in the form of a control panel.

Figure 2:
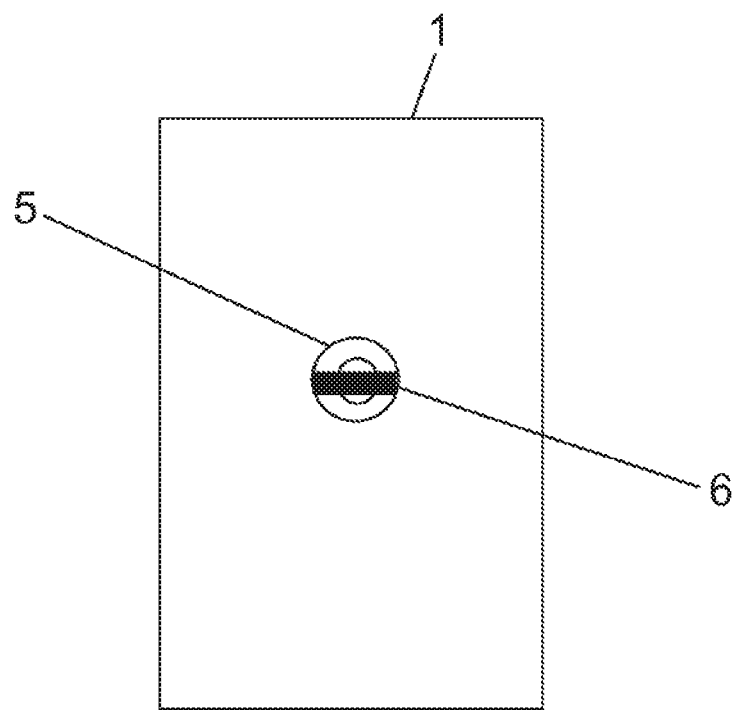
FIG. 2 shows a detail from FIG. 1 in an enlarged illustration.

FIG. 2 shows one of the EMS electrodes 1 viewed outward from the interior of the pants leg, wherein an electrically conductive layer facing toward the body has been removed, so that the rear side of the snap 5 can be seen, onto which a sacrificial anode 6 in the form of a magnesium strip is adhesively bonded.

Figure 3:
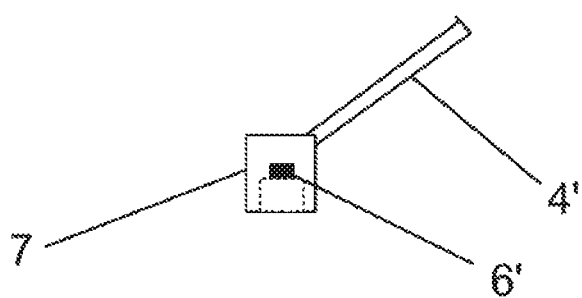
FIG. 3 shows an EMS signal cable.

In an alternative or additional exemplary embodiment of the invention, instead of a standard EMS signal cable 4, an EMS signal cable 4' shown in FIG. 3 is used, which is provided with a sacrificial anode 6'. In the exemplary embodiment shown in FIG. 3, the sacrificial anode 6' is integrated in this case into a plug 7, which can be plugged into one of the snaps 5 or a corresponding snap of an EMS electrode, to connect the EMS electrode to the EMS stimulus generating unit 3.

Figure 4:
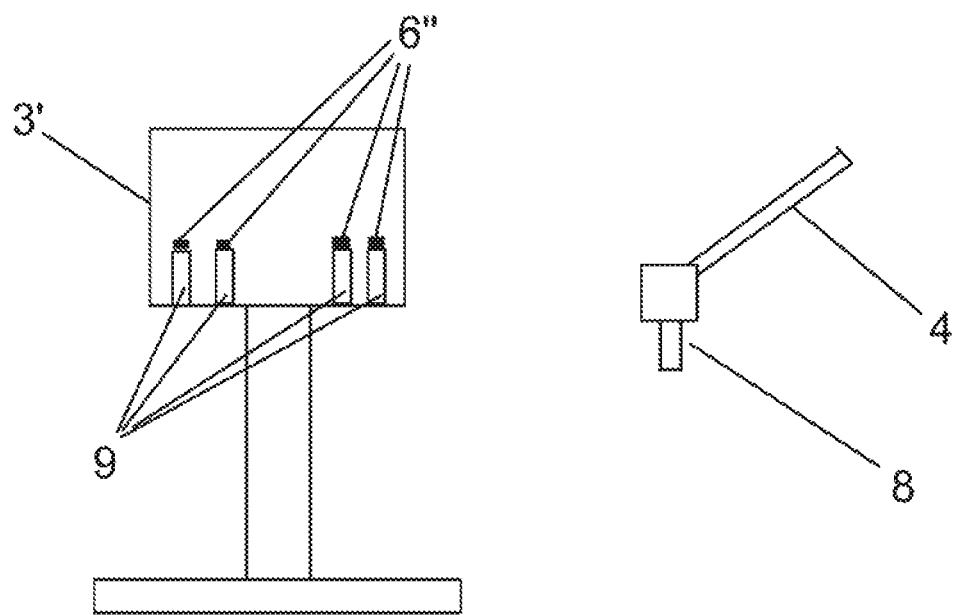
FIG. 4 shows a schematic illustration of an EMS stimulus generating unit having an assigned EMS signal cable.

In a further exemplary embodiment of the invention, an EMS stimulus generating unit 3', which is schematically illustrated in FIG. 4, is provided, which is also installed in an external formation like a control panel, but in contrast to the EMS stimulus generating unit 3 shown in FIG. 1, has a socket 9 for each of the EMS signal cables or the end thereof is provided with a plug 8, in which a sacrificial anode 6" is arranged, preferably replaceably arranged.

It is understood that the foregoing description is that of the exemplary embodiments of the invention and that various changes and modifications may be made thereto without departing from the spirit and scope of the invention as defined in the appended claims.

What is claimed is:

1. An electrical muscle stimulation (EMS) garment comprising:
   a clothing material formed into the EMS garment;
   at least one EMS electrode connected to the clothing material and configured to transmit EMS stimuli generated by an EMS stimulus generating unit to a living body, the at least one EMS electrode being at least one of a plane pad configured to be applied flexibly to the living body or an electrically conductive textile layer containing metallic or metallized threads, the EMS stimuli including current pulses and/or an alternating current, the alternating current having predefined values, the predefined values including a predefined amplitude value and a predefined frequency value
   at least one electrical terminal formed as at least one snap, wherein each of the at least one electrical terminal is connected to one of the at least one EMS electrode via one EMS signal line pressed to, sewn on, soldered on, or welded on the at least one electrical terminal;
   at least one sacrificial anode, wherein each sacrificial anode is connected electrically conductively to the at least one EMS electrode, riveted on the at least one snap, and is made of a material having a negative standard electrode potential in an electrochemical electromotive series or includes the material having the negative standard electrode potential in the electrochemical electromotive series; and
   at least one EMS signal cable, wherein each EMS signal cable is configured to connect the EMS garment to the EMS stimulus generating unit and is connectable to the at least one electrical terminal.

2. The EMS garment of claim 1, wherein the clothing material is formed into at least one of a suit, a jacket, a belt, a shirt, a pair of pants, a wristband, and a leg band.

3. The EMS garment of claim 1, wherein:
   the at least one EMS electrode is the electrically conductive textile layer containing the metallic or metallized threads;
   the at least one EMS electrode supports another of the at least one sacrificial anode, and
   the at least one sacrificial anode is connected electrically conductively to the electrically conductive textile layer of the at least one EMS electrode.

4. The EMS garment of claim 3, wherein:
   the at least one EMS electrode supports another of the at least one sacrificial anode is the EMS electrode sewn-on the EMS garment and/or the EMS electrode incorporated into the EMS garment, and
   the at least one EMS electrode incorporated into the EMS garment is the EMS electrode knitted, crocheted, or weaved into the EMS garment.

5. The EMS garment of claim 1, wherein:
   the EMS signal line, which connects the at least one electrical terminal with the at least one EMS electrode, is configured as conductor tracks, and
   the conductor tracks are conductor tracks knitted or woven into the EMS garment.

6. The EMS garment of claim 1, wherein:
   the at least one sacrificial anode has a shape of a plate, and
   the at least one sacrificial anode is riveted by one or more rivets on the EMS garment.

7. The EMS garment of claim 1, wherein the sacrificial anode is formed as a rivet.

8. The EMS garment of claim 1, wherein:
   the material having the negative standard electrode potential in the electrochemical electromotive series, of which the at least one sacrificial anode is made or which the sacrificial anode includes, is magnesium or a magnesium alloy, and
   the material is free of nickel.

* * * * *